(12) United States Patent
Kawamura et al.

(10) Patent No.: US 11,787,855 B2
(45) Date of Patent: Oct. 17, 2023

(54) EGG, FERTILIZED EGG, OR EMBRYO QUALITY IMPROVING AGENT

(71) Applicant: MPO, INC., Kawasaki (JP)

(72) Inventors: Kazuhiro Kawamura, Kanagawa (JP); Yuta Kawagoe, Kanagawa (JP)

(73) Assignee: MPO, INC., Kawasaki (JP)

( * ) Notice: Subject to any disclaimer, the term of this patent is extended or adjusted under 35 U.S.C. 154(b) by 732 days.

(21) Appl. No.: 16/336,689

(22) PCT Filed: Sep. 26, 2017

(86) PCT No.: PCT/JP2017/034703
§ 371 (c)(1),
(2) Date: Mar. 26, 2019

(87) PCT Pub. No.: WO2018/056461
PCT Pub. Date: Mar. 29, 2018

(65) Prior Publication Data
US 2021/0095015 A1    Apr. 1, 2021

(30) Foreign Application Priority Data

Sep. 26, 2016  (JP) ................................ 2016-187532

(51) Int. Cl.
| | |
|---|---|
| *C07K 16/24* | (2006.01) |
| *C07K 16/28* | (2006.01) |
| *C12N 5/073* | (2010.01) |
| *G01N 33/68* | (2006.01) |

(52) U.S. Cl.
CPC .......... *C07K 16/24* (2013.01); *C07K 16/2866* (2013.01); *C12N 5/0604* (2013.01); *G01N 33/689* (2013.01); *G01N 33/6863* (2013.01); *C12N 2501/998* (2013.01); *G01N 2333/521* (2013.01); *G01N 2800/36* (2013.01); *G01N 2800/7042* (2013.01)

(58) Field of Classification Search
CPC ............ C07K 2317/76; C07K 16/2866; C07K 16/24; G01N 33/6863; G01N 33/689; C12N 5/0604
See application file for complete search history.

(56) References Cited

U.S. PATENT DOCUMENTS

2011/0027266 A1   2/2011   Lee et al.

FOREIGN PATENT DOCUMENTS

| JP | 2005-527189 | | 9/2005 |
| JP | 2010-537636 | A | 12/2010 |
| WO | WO 03/047420 | A2 | 6/2003 |
| WO | WO-2005/019440 | A1 | 3/2005 |
| WO | WO-2007/150015 | A2 | 12/2007 |

OTHER PUBLICATIONS

Wente et al. Cancer Letters, 2006, 241(2):221-227 (Year: 2006).*
Cheng et al. Potential roles and targeted therapy of the CXCLs/CXCR2 axis in cancer and inflammatory diseases. BBA—Reviews on Cancer 1871 (2019) 289-312 (Year: 2019).*
Bowie et al. Deciphering the Message in Protein Sequences: Tolerance to Amino Acid Substitutions. Science, 1990, 247:1306-1310 (Year: 1990).*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111:2129-2138, 1990 (Year: 1990).*
Lazar et al. Transforming Growth Factor alpha: Mutation of Aspartic Acid 47 and Leucine 48 Results in Different Biological Activities Mol. Cell. Biol., 8:1247-1252, 1988 (Year: 1988).*
Bork. Powers and Pitfalls in Sequence Analysis: The 70% Hurdle. Genome Research, 2000, 10:398-400 (Year: 2000).*
Vajdos et al. Comprehensive Functional Maps of the Antigen binding Site of an Anti-ErbB2 Antibody Obtained with Shotgun Scanning Mutagenesis. J Mol Biol. Jul. 5, 2002;320(2):415-28 (Year: 2002).*
Brown et al. Tolerance to Single, but Not Multiple, Amino Acid Replacements in Antibody VH CDR2. J Immunol. May 1996; 156(9):3285-91 (Year: 1996).*
Guido et al. Virtual Screening and Its Integration with Modern Drug Design Technologies. Curr Med Chem. 2008; 15(1):37-46 (Year: 2008).*
Clark et al. Discovery and Development of Janus Kinase (JAK) Inhibitors for Inflammatory Diseases. J. Med. Chem., 2014, 57 (12), pp. 5023-5038 (Year: 2014).*
Kang et al. CXCR2-Mediated Granulocytic Myeloid-Derived Suppressor Cells' Functional Characterization and Their Role in Maternal Fetal Interface. DNA Cell Biol. Jul. 2016;35(7):358-65. doi: 10.1089/dna.2015.2962. Epub Mar. 30, 2016 (Year: 2016).*
Dominguez et al. Fertility and Sterility, 2010; 93(3): 774-783 (Year: 2010).*
Notification of Transmittal of Copies of Translation of the International Preliminary Report on Patentability (IPRP) from corresponding PCT Application No. PCT/JP2017/034703, dated Apr. 4, 2019.
Aihua Li et al., Angiogenesis, Kluwer Academic Publishers, DO, vol. 8, No. 1, Mar. 1, 2005. pp. 63-71.
Hideki Igarashi et al., Reproductive Medicine and Biology, Springer Japan, Tokyo, vol. 14, No. 4, May 9, 2015, pp. 159-169.
Vittorio Unfer et al., Gynecological Endocrinology: The Official Journal of the International Society of Gynecological Endocrinology, London: Informa Healthcare, GB, vol. 27, No. 11, Nov. 1, 2011, pp. 857-861.

(Continued)

*Primary Examiner* — Vanessa L. Ford
*Assistant Examiner* — Sandra Dillahunt
(74) *Attorney, Agent, or Firm* — Harness, Dickey & Pierce, P.L.C.

(57) ABSTRACT

Object of the present invention is to provide means for improving the quality of preimplantation embryos deteriorated with age or the like. The present invention relates to an agent for improving the quality of an egg, a fertilized egg, and/or an embryo, including a substance that inhibits signal transmission from CXCL5.

5 Claims, 13 Drawing Sheets

(56) References Cited

OTHER PUBLICATIONS

B. W. Whitcomb et al., American Journal of Epidemiology, vol. 166, No. 3, May 29, 2007, pp. 323-331.
Dorothea M. Wunder et al., Acta Obstetricia et Gynecologica, vol. 85, No. 3, Jan. 1, 2006, pp. 336-342.
Dessie Salilew-Wondim et al., Physiological Genomics, vol. 42, Apr. 13, 2010, pp. 201-218, Retrieved from the Internet: URL:https://journals.physiology.org/doi/pdf/10.1152/physiolgenomics.00047.2010, (retrieved on May 18, 2020).
Bruno Ramalho de Carvalho et al., ISRN Obstetrics and Gynecology, vol. 2012, Jan. 1, 2012, pp. 1-10.
Xiaomin Kang et al., DNA and Cell Biology, vol. 35, No. 7, Jul. 1, 2016, pp. 358-365.
Dongcai Wu et al., Placenta, W. B. Saunders, GB, vol. 43, Apr. 20, 2016, pp. 17-25.
E. Dimitriadis et al., Human Reproduction Update, vol. 11, No. 6, Aug. 25, 2005, pp. 613-630.
Mei-Rong Du et al., Cellular & Molecular Immunology, vol. 11, No. 5, Aug. 11, 2014, pp. 438-448.
Rosanna Ramhorst et al., Cell Adhesion & Migration, vol. 10, No. 1-2, Feb. 18, 2016, pp. 197-207.
Extended European Search Report dated Jun. 2, 2020 issued in the corresponding European patent Application No. 17853228.9.
Dominguez, Francisco et al. (2010) "Embryologic outcome and secretome profile of implanted blastocysts obtained after coculture in human endometrial epithelial cells versus the sequential system.", *Fertility and Sterility*, vol. 93, No. 3, pp. 774-782, 782.e1, ISSN: 015-0282.
Kawagoe, Y., et al. (2017) "Inhibition of CXCL5-CXCR2 Signaling Improves the Implantation of Aging Embryos for Pregnancy.", *Fertility and Sterility*, vol. 108, Issue.3, Supplement,p.e372, particularly, P-695.
Zhang, Ruopeng, et al. (2016) "RNA-Seq-Based Transcriptome Analysis of Changes in Gene Expression Linked to Human Pregnancy Outcome After In Vitro Fertilization-Embryo Transfer.", Reproductive Sciences, vol. 23(1), pp. 134-145, ISSN: 1933-7191.
International Search Report, dated Nov. 7, 2017, issued in International Patent Application No. PCT/JP2017/034703, with English translation.
Office Action from corresponding Japanese Patent Application No. 2018-540349, dated May 10, 2022.
Capucetti, A., et al.; "Multiple Roles for Chemokines in Neutrophil Biology", Frontiers in Immunology, 2020, vol. 11, Article 1259, pp. 1-9.
Matsuo, K., et al.; "Chemokine receptors and cell migration", Japanese Journal of Thrombosis and Hemostasis, vol. 30 (4), pp. 610-618, 2019.
Office Action from corresponding Chinese Patent Application No. 201780059256.1, dated Jun. 29, 2022.
Zhang Lingmei, "Effects of follicular fluid of patients with endometriosis on egg development and fertilization in mice and changes of ENA78 in follicular fluid", Full text database of Chinese excellent master's thesis: Medical and Health Science and Technology Series, issue 07, E068-8 (2010).

* cited by examiner

EGG, FERTILIZED EGG, OR EMBRYO QUALITY IMPROVING AGENT

CROSS-REFERENCE TO RELATED APPLICATIONS

This application is a national phase application of PCT Application No. PCT/JP2017/034703, filed on 26 Sep. 2017, which claims benefit of Japanese Patent Application 2016-187532, filed on 26 Sep. 2016. The entire disclosure of the applications identified in this paragraph are incorporated herein by references.

FIELD

The present invention relates to an agent for improving the quality of an egg, a fertilized egg, and/or an embryo, including a substance that inhibits signal transmission from CXCL5.

BACKGROUND

In general, cells constituting the human body repeatedly divide and proliferate as the body grows, and in such repetitions, cells are exposed to various stresses associated with aging and accumulate damage. This is considered to be due to oxidative damage due to accumulation of active oxygen, DNA damage due to ultraviolet rays, or the like, resulting in malfunction of mitochondria, dysfunction of intracellular metabolism, or the like, leading to canceration/cell death. The fact that the quality of cell declines with age is thus a phenomenon common to all mortal organisms including humans. Until now, it is inevitable that the quality of cell deteriorates with age, and research for delaying/stopping/improving deterioration of the quality of cell is widely conducted.

In the field of reproductive medicine, attention is paid to the fact that the quality of preimplantation embryo deteriorates with age. Deterioration of the quality of preimplantation embryo leads to a decreased pregnancy rate or an increased miscarriage rate due to implantation failure. Indeed, the incidence of infertility by age is 6% in the first half of the 20's, and starts to increase sharply in the 30's, reaching 64% in the 40's. Among in vitro fertilization cases in Japan, 55% are aged cases of 38 years of age or older. While the pregnancy rate of in vitro fertilization cases of young patients is 26% on average, the pregnancy rate decreases in aged cases and is only 6.3% for cases of 38 years of age or older.

CXCL5 is a kind of chemokine, which contributes to chemotaxis/activation of neutrophils, and is known to be involved in inflammatory reaction (Patent Document 1).

PRIOR ART DOCUMENTS

Patent Document

[Patent Document 1] Japanese Translation of PCT International Application Publication No. 2005-527189

SUMMARY OF THE INVENTION

Technical Problem

Attempts have been made to improve the quality of a preimplantation embryo deteriorated with age, but methods with high effectiveness have not been developed. As a result, pregnancy is performed not by own embryo, but by in vitro fertilization/embryo transplantation of an egg provided by a young woman.

In such a pregnancy with an egg provided, an ethical problem is pointed out to fertilize an egg of another person and a sperm of a husband, transplant the preimplantation embryo into the uterus, and pregnant. There is also a view that immune abnormality occurs in a mother's body by pregnancy of a completely non-self child, and pregnancy complications increase. Furthermore, egg donors also need to receive highly invasive actions such as frequent injections and egg collection for ovarian stimulation, and safety problems are pointed out.

On the other hand, attempts have been made to improve the quality of preimplantation embryos by using supplements that may reduce oxidative stress and inflammatory damage, but scientifically proven highly effective supplements have not been found. In other words, means for improving preimplantation embryos deteriorated with age or the like are demanded.

In order to meet these demands, the present invention aims to provide means for improving the quality of preimplantation embryos deteriorated with age or the like.

Solution to Problem

The present inventors conducted intensive studies to solve the above-described problems. As a result, it was found that CXCL5 which is a kind of chemokine induces aging of embryos, and found that inhibition of signal transmission from CXCL5 can improve the quality of preimplantation embryo deteriorated due to age or the like. Based on the findings, the present invention has been completed.

That is, the present invention relates to the following.

[1] An agent for improving a quality of an egg, a fertilized egg, and/or an embryo, including a substance that inhibits signal transmission from CXCL5.

[2] The agent according to [1], wherein the substance that inhibits signal transmission from CXCL5 is a substance that inhibits an interaction between CXCL5 and CXCR2.

[3] The agent according to [2], wherein the substance that inhibits an interaction between CXCL5 and CXCR2 is an anti-CXCL5 antibody or a fragment thereof, an anti-CXCR2 antibody or a fragment thereof, or a CXCR2 antagonist.

[4] The agent according to any one of [1] to [3], wherein the quality of an egg, a fertilized egg, and/or an embryo is deteriorated due to aging.

[5] A culture medium of an egg, a fertilized egg, and/or an embryo, containing the agent according to any one of [1] to [4].

[6] A method of predicting aging of an egg, a fertilized egg, and/or an embryo, including a step of determining a presence or absence of aging of an egg, a fertilized egg, and/or an embryo by using a concentration of CXCL5 in a serum isolated from a subject as an index.

[7] A method of predicting aging of an egg, a fertilized egg, and/or an embryo, including a step of determining a presence or absence of aging of an egg, a fertilized egg, and/or an embryo using a concentration of CXCL5 in an ovarian tissue isolated from a subject as an index.

[8] A method of improving a quality of an egg, a fertilized egg, or an embryo, including a step of bringing an egg, a fertilized egg, or an embryo into contact with a substance that inhibits signal transmission from CXCL5.

[9] A method of culturing an egg, a fertilized egg, or an embryo, including a step of culturing an egg, a fertilized egg, or an embryo in a culture medium containing a substance that inhibits signal transmission from CXCL5.

Advantageous Effects of the Invention

According to the present invention, by inhibiting CXCR2-mediated signal transmission from CXCL5, the quality of an egg, a fertilized egg, or an embryo deteriorated due to aging or the like can be improved, and pregnancy rate/fertility rate in in vitro fertilized embryo transplantation or the like can be increased. Aging of an egg, a fertilized egg, or an embryo can be predicted by using the concentration of CXCL5 in blood or an ovarian tissue as a biomarker.

DESCRIPTION OF THE EMBODIMENTS

Quality Improving Agent

Figure 1:
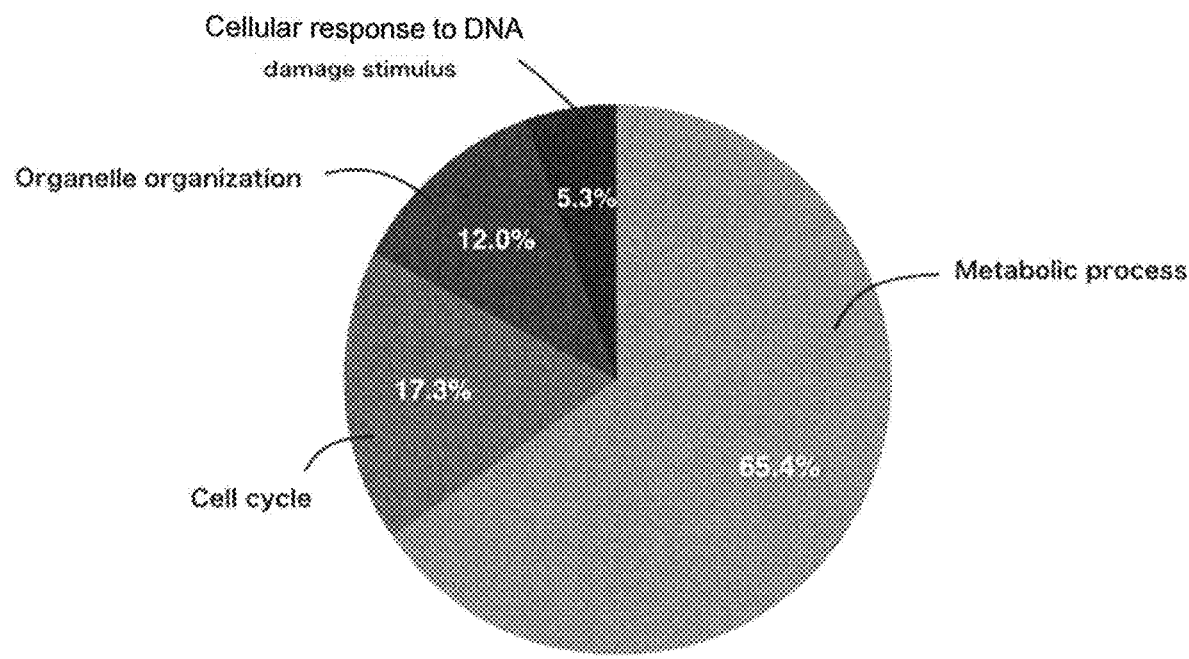
FIG. 1 is a diagram showing results of biological function analysis of genes whose expression was varied by gene expression comparison of blastocysts of young infertile patients and elderly infertile patients.

One embodiment of the present invention relates to an agent for improving the quality of an egg, a fertilized egg, and/or an embryo, including a substance that inhibits signal transmission from CXCL5 (hereinafter, sometimes simply referred to as "quality improving agent"). In other words, the present invention is characterized in that a substance that inhibits signal transmission from CXCL5 is used for improving the quality of an egg, a fertilized egg, and/or an embryo. "Improving the quality of an egg, a fertilized egg, and an embryo" can be rephrased as "improving the pregnancy ability of an egg, a fertilized egg, and an embryo."

As shown in the Examples below, the present inventors revealed that the concentration of CXCL5 in ovaries increases due to aging and the like. It was found that CXCL5 induces aging of an egg, a fertilized egg, an embryo, and the like, resulting in deteriorated quality of the embryo. Furthermore, it was found that the quality of an egg, a fertilized egg, or an embryo deteriorated by CXCL5 can be improved by inhibiting signal transmission from CXCL5 via CXCR2 which is a chemokine receptor. Based on the findings, the present invention has been completed.

In other words, the agent for improving the quality of an egg, a fertilized egg, and/or an embryo of the present invention is a substance that inhibits signal transmission from CXCL5, and is not particularly limited as long as the substance exerts action of improving the quality of an egg, a fertilized egg, or an embryo. Examples thereof include a substance that inhibits an interaction between CXCL5 and CXCR2.

Examples of the substance that inhibits an interaction between CXCL5 and CXCR2 include an anti-CXCL5 antibody or a fragment thereof, an anti-CXCR2 antibody or a fragment thereof, and a CXCR2 antagonist. These can be used alone or in combination of two or more kinds thereof.

Examples of the anti-CXCL5 antibody, anti-CXCR2 antibody or a fragment thereof include an antibody (neutralizing antibody) that inhibits an interaction between CXCL5 and CXCR2 by linking to CXCL5 or CXCR2 or a fragment thereof.

As the anti-CXCL5 antibody and anti-CXCR2 antibody, a known one can be used. Although not particularly limited, examples of the anti-CXCL5 antibody include Anti-CXCL5 antibody (abcam, R and D systems, LifeSpan Biosciences, ThermoFisher SCIENTIFIC). Although not particularly limited, examples of the anti-CXCR2 antibody include Anti-CXCR2 antibody (abcam), Human CXCR2/IL-8RB Mab (R and D systems), Mouse Monoclonal CXCR2/IL-8 RB Antibody (Novuss Biologicals), CXCR2/IL8RB antibody (ThermoFisher SCIENTIFIC).

The anti-CXCL5 antibody can also be produced by a conventional method using CXCL5 or a fragment thereof as an antigen, and such an antibody can be used in the present invention.

The anti-CXCR2 antibody can also be produced by a conventional method using CXCR2 or a fragment thereof as an antigen, and such an antibody can be used in the present invention.

The antibody may be a polyclonal antibody or a monoclonal antibody.

The antibody may be a complete antibody molecule or an antibody fragment capable of specifically linking to an antigen, such as Fab (fragment of antigen binding), F(ab')2, Fab', Fv, scFv (single chain Fv), dsFv (disulfide stabilized Fv), CDR (complementarity determining region). A human chimeric antibody or a humanized antibody can also be used as the antibody.

Example of the CXCR2 antagonist include a substance that inhibits an interaction between CXCL5 and CXCR2 by competing with CXCL5 and links to CXCR2 and does not itself have the ability to activate CXCR2.

As the CXCR2 antagonist, a known CXCR2 antagonist can be used. Although not particularly limited, examples thereof include SB225002(TOCRIS).

Antibodies and antagonists that inhibit an interaction between CXCL5 and CXCR2 preferably inhibit linking of CXCL5 and CXCR2 to 50% or less, 40% or less, 30% or less, 20% or less, 10% or less, or 1% or less as compared with linking in the absence of antibody and antagonist. Antibodies and antagonists to be used in the present invention can be selected by a known method using CXCL5 and CXCR2 as indices as to whether or not to inhibit linking of CXCL5 and CXCR2. By inhibiting linking of CXCL5 and CXCR2, CXCR2-mediated signal transmission from CXCL5 is inhibited, and the quality of an egg, a fertilized egg, or an embryo deteriorated by aging or the like can be improved. Antibodies and antagonists used in the present invention also can be selected by a known method using CXCL5 and CXCR2 as indices as to whether or not to inhibit CXCR2-mediated signal transmission from CXCL5.

By bringing the agent for improving the quality of an egg, a fertilized egg, and/or an embryo of the present invention into contact with an egg, a fertilized egg, or an embryo, CXCR2-mediated signal transmission from CXCL5 is inhibited, and the quality of an egg, a fertilized egg, or an embryo deteriorated by CXCL5 is improved. Examples of the method of bringing the agent for improving the quality of an egg, a fertilized egg, and/or an embryo of the present invention in contact with an egg, a fertilized egg, or an embryo include a method of adding the quality improving agent of the present invention to a culture medium and culturing the egg, the fertilized egg, or the embryo in the same culture medium. Improvement of embryo quality in the present invention includes: improvement of embryo quality by improving the quality of an egg and/or a fertilized egg by bringing the quality improving agent of the present invention into contact with the egg and/or the fertilized egg; and improvement of embryo quality by bringing the quality improving agent of the present invention into contact with an embryo. Similarly, the quality improvement of a fertilized egg in the present invention includes: quality improvement of a fertilized egg by improving the quality of an egg by bringing the quality improving agent of the present invention into contact with the egg; and quality improvement of a fertilized egg by bringing the quality improving agent of the present invention into contact with the fertilized egg.

A quality improvement action of an egg, a fertilized egg, or an embryo of the present invention can be confirmed when one or more evaluation items related to pregnancy/childbirth such as a blastocyst reaching rate, an implantation rate, an offspring acquisition rate, or a miscarriage rate in a group to which the quality improving agent of the present invention is added in an in vitro culture system or the like which is usually used is improved compared with a group to which no quality improving agent is added.

The subject to which the agent for improving the quality of an egg, a fertilized egg, or an embryo of the present invention is applied is not particularly limited as long as the subject is a subject whose quality of an egg, a fertilized egg, or an embryo is deteriorated due to aging or the like and which is demanded to be improved. Examples thereof include: a subject whose quality of an egg, a fertilized egg, or an embryo is deteriorated due to secretion or increased secretion of CXCL5 with aging; and a subject whose pregnancy rate/fertility rate or the like deteriorated due to such deterioration of an egg, a fertilized egg, or an embryo. The subject is a mammal and examples of the mammal include, but are not limited to, a human, and a non-human animal such as an animal having commercial value for meat and dairy production such as a pig, a cattle, a bovid, a horse, or a water buffalo.

Culture Medium

One embodiment of the present invention relates to a culture medium of an egg, a fertilized egg, and/or an embryo containing an agent for improving the quality of an egg, a fertilized egg, and/or an embryo composed of a substance that inhibits signal transmission from CXCL5 (hereinafter, sometimes simply referred to as "culture medium"). The culture medium of an egg, a fertilized egg, and/or an embryo of the present invention is characterized by containing the agent for improving the quality of an egg, a fertilized egg, and/or an embryo of the present invention, and can be used to improve the quality of an egg, a fertilized egg, and/or an embryo that is deteriorated due to secretion and increased secretion of CXCL5 with aging or the like during culturing the egg, the fertilized egg, or the embryo.

The culture medium of the present invention is not particularly limited as long as the medium contains the agent for improving the quality of an egg, a fertilized egg, and/or an embryo of the present invention as an effective ingredient. For example, the culture medium of the present invention can be produced by adding the agent for improving the quality of an egg, a fertilized egg, and/or an embryo of the present invention to a known culture medium of an egg, a fertilized egg, or an embryo.

As the culture medium of an egg, a fertilized egg, or an embryo to be used for in vitro fertilization or the like, culture media of different compositions can be used depending on the stage of development or the like. There is no particular limitation as long as the medium is a culture medium which is conventionally used for culturing an egg, a fertilized egg, or an embryo, and the culture medium of the present invention can be produced by addition of the agent for improving the quality of an egg, a fertilized egg, and/or an embryo of the present invention. An embodiment in which the quality improving agent of the present invention is added to a culture medium used for culturing a fertilized egg and a culture medium used for culturing an embryo from the morula stage to the blastocyst stage is preferable.

More specifically, a first culture medium used for culturing an embryo from fertilization and postfertilization of a sperm and an egg (pronuclear stage) to 16 cell stage, a second culture medium used for culturing an embryo from the morula stage to the blastocyst stage, and the like are used as a culture medium for an egg, a fertilized egg, or an embryo used for in vitro fertilization or the like. For the first culture medium and the second culture medium, the same culture medium may be used. For collection of a sperm and collection of an egg, the first culture medium can be used. These culture media are commercially available, and a commercially available culture medium can also be used for producing the culture medium of the present invention. Although not particularly limited, as the first culture medium, in addition to a culture medium for laboratory animals, Sydney IVF Fertilization medium (Cook medical), Sydney IVF Cleavage medium (Cook medical), Sequential Fert (ORIGIO), Sequential Cleav (ORIGIO), Universal IVF medium (ORIGIO), G-IVFTM (Vitrolife), G-1TM v5 (Vitrolife), or the like can be used, and as the second culture medium, in addition to a culture medium for laboratory animals, Sydney IVF Blastosist medium (Cook medical), Seaquential Blast (ORIGIO), Blastassist medium (ORIGIO), G-2TM v5 (Vitrolife), or the like can be used.

The culture medium of the present invention can also be produced using a culture medium prepared by dissolving an inorganic salt, a saccharide, an amino acid, a cytoprotective substance, an antibiotic, a physiologically active substance, and the like in ultra pure or distilled water or the like.

In the case of an antibody or a fragment thereof, the content of the agent for improving the quality of an egg, a fertilized egg, and/or an embryo of the present invention in a culture medium, as the concentration in the culture medium, is usually from 0.01 to 100 µg/ml, and preferably from 0.1 to 10 µg/ml. In the case of an antagonist, the content can usually be from 1 to 100 nM, and preferably from 10 to 30 nM. When an antibody or a fragment thereof and an antagonist are used in combination, the content can be usually from 28.6:1 to 2857.1:1, and preferably from 28.6:1 to 1,000:1 (mass ratio).

Cultivation of an egg, a fertilized egg, or an embryo can be carried out according to a known culture method except that the culture medium of the present invention is used. Conditions for culturing are exemplified below, but the culture conditions are not limited thereto, and can be appropriately changed in accordance with an object to be applied, a required effect, and the like.

Cultivation temperature can usually be 37° C. or higher. The culture gas phase can be a gas phase of usually 5% $CO_2$ and 95% $O_2$.

The culture time can be usually from 1 hour to 2 hours in the case of pre-culture of an egg for in vitro fertilization, usually from 5 to 72 hours in the case of a fertilized egg, and usually from 72 to 144 hours in the case of an embryo after morula stage.

The quality improving agent of the present invention can be brought into contact with an egg, a fertilized egg, or an embryo during at least one of the period of preculture of an egg, the period of culture of a fertilized egg, and the period of culture of an embryo at or after the morula stage.

The quality improving agent of the present invention may be brought into contact with an egg, a fertilized egg, or an embryo over a plurality of culture periods. The time for bringing the quality improving agent of the present invention into contact with an egg, a fertilized egg, or an embryo may be all or part of each period.

The culture medium of an egg, a fertilized egg, and/or an embryo of the present invention is not particularly limited, and is intended for an egg, a fertilized egg, and an embryo of a mammal requiring improvement of the quality of an egg, a fertilized egg, or an embryo that is deteriorated due to aging or the like, improvement of declined success rate of in vitro fertilization/intracytoplasmic sperm injection by an egg, a fertilized egg, or an embryo, or the like. The subject is a mammal and examples of the mammal include, but are not limited to, a human, and a non-human animal such as a pig, a cattle, a bovid, a horse, or a water buffalo.

Method of Predicting Aging

One embodiment of the present invention relates to a method of predicting aging of an egg, a fertilized egg, and/or an embryo, including determining the presence or absence of aging of an egg, a fertilized egg, and/or an embryo by using the concentration of CXCL5 in a serum isolated from a subject as an index. Another embodiment of the present invention relates to a method of predicting aging of an egg, a fertilized egg, and/or an embryo, including determining the presence or absence of aging of an egg, a fertilized egg, and/or an embryo using the concentration of CXCL5 in an ovarian tissue isolated from a subject as an index (hereinafter, each of the methods is sometimes simply referred to as "method of predicting aging").

As shown in the Examples below, it was revealed that the concentration of CXCL5 in an ovary correlated with the degree of the concentration of CXCL5 in a serum. Therefore, in addition to using the CXCL5 concentration in the ovary as an index, by using the concentration of CXCL5 in the serum as an index, it is possible to predict the concentration of CXCL5 in the ovary and whether or not an egg, a fertilized egg, or an embryo is subjected to induction of aging by CXCL5.

Examples of blood used as a specimen in the present invention include a serum, and a serum can be appropriately obtained by treating blood collected from a subject according to a conventional method.

Examples of the ovarian tissue to be used as a specimen in the present invention include an ovarian tissue itself, an ovarian tissue preparation, an ovarian tissue-derived component (an ovary cell, a follicular fluid, a granule membrane cell, or the like), and these can be appropriately obtained by treating ovarian tissue collected from a subject according to a conventional method.

The concentration of CXCL5 in the ovarian tissue is not limited to the concentration of CXCL5 protein, and may be the concentration of a substance related to CXCL5 expression or the like. Here, the expression means transcription of the gene of CXCL5 or translation from a transcription product of the gene.

The method for measuring the concentration of CXCL5 in a serum or an ovarian tissue is not particularly limited, and examples thereof include various chromatographic methods such as an immunochemical method and an HPLC method. When the related substance is a nucleic acid, examples of the method for measuring the concentration of CXCL5 include a PCR method such as a RT-PCR method. From the viewpoint of convenience and the like, it is preferable to measure by an immunochemical method using an antibody that recognizes CXCL5.

The immunochemical method used for measuring the concentration of CXCL5 in a serum or an ovarian tissue is not particularly limited, and examples of a known method include an enzyme immunoassay (EIA method), a latex agglutination method, an immunochromatography, a radioimmunoassay (RIA method), a fluorescence immunoassay (FIA method), a luminescence immunoassay, a spin immunoassay, a turbidimetric method for measuring the turbidity associated with formation of an antigen-antibody complex, an enzyme sensor electrode method for detecting a potential change due to linking with an antigen using an antibody solid phase membrane electrode, an immunoelectrophoresis, and a Western blotting method. From the viewpoint of convenience and the like, it is preferable to measure by an EIA method, a latex agglutination method, or an immunochromatography method.

The EIA method includes a competitive method of competing an enzyme-labeled antigen with an antigen in a specimen, and a noncompetitive method of not competing with each other, and among these, a sandwich enzyme-linked immune solid-phase assay (sandwich ELISA) which is a non-competitive method using two kinds of antibodies is preferable in terms of ease of operation and the like.

When the concentration of CXCL5 in a serum or an ovarian tissue is used as an index, for example, the concentration of CXCL5 in the serum or ovarian tissue of the same type of control as a subject (such as a healthy subject or a young subject) is set as a cutoff value, or a cutoff value is set based on the concentration. The cutoff value can be appropriately set as the concentration of CXCL5 in a control serum or an ovarian tissue or a value based on the concentration according to a specimen, a required effect, or the like based on a conventional method.

When the concentration of CXCL5 in a serum or an ovarian tissue isolated from a subject is higher than the cutoff value or a preset cutoff value, it is determined that the egg, the fertilized egg, or the embryo is aged. When the concentration of CXCL5 in a serum or an ovarian tissue isolated from a subject is the same as or lower than a cutoff value, it is determined that the egg, the fertilized egg, or the embryo is not aged. Aging thus can be predicted. The degree of aging can be predicted by comparing the concentration of CXCL5 in a serum or an ovarian tissue isolated from a subject to a cutoff value.

The object of application of the method of predicting aging of the present invention is a mammal, and is not particularly limited. The mammal is not particularly limited, and examples thereof include a human, and a non-human animal such as a pig, a cattle, a bovid, a horse, or a water buffalo.

Quality Improvement Method and Culture Method

Furthermore, the present invention includes a method for improving the quality of an egg, a fertilized eggs, or an embryo, including a step of contacting the egg, the fertilized egg, or the embryo with a substance that inhibits signal transmission from CXCL5. The present invention includes a method for improving the quality of an egg, a fertilized egg, or an embryo and increasing the pregnancy rate/fertility rate, including a step of bringing the egg, the fertilized egg, or the embryo into contact with a substance that inhibits signal transmission from CXCL5. For the contact method or the like, the contents of the above section can be referred to.

Furthermore, the present invention includes a method of culturing an egg, a fertilized egg, or an embryo, including a step of culturing the egg, the fertilized egg, or the embryo in a culture medium containing a substance that inhibits signal transmission from CXCL5. For the conditions of cultivation or the like, the contents of the above section can be referred to.

EXAMPLES

Hereinafter, the present invention will be described in detail with reference to Examples, but the present invention is not limited to the following Examples.

Example 1

Gene expression profiles were compared in preimplantation embryos of young infertile patients and preimplantation embryos of elderly infertile patients of 39 years of age or older, and genes that differed in expression were comprehensively analyzed. Among them, those which are secretion factors and which are highly expressed in elderly patients were searched and used as candidate factors involved in deterioration of the quality of embryo due to aging. Specifically, an experiment was carried out as follows.

Gene expression of blastocysts in young patients and elderly patients was comprehensively compared by DNA microarray, and as a result, there were 3,789 differentially expressed genes of 5 times or more in expression level. As a result of biological function analysis of these genes, genes involved in metabolism, cell cycle, or the like were affected by aging (FIG. 1).

From among differentially expressed genes, those which were secretion factors and which were highly expressed in elderly patients were extracted, and CXCL5 showing expression levels 202.8 times higher in blastocysts of elderly patients compared with young patients was regarded as an eventual candidate factor.

Example 2

Whether the candidate factor CXCL5 obtained in Example 1 improved the quality of embryo deteriorated by aging by addition of a neutralizing antibody or an antagonist of a specific receptor in an in vitro culture system of an aged mouse embryo or not was examined. Ovulated mature eggs were collected from 42-week-old aged mice and subjected to in vitro fertilization, the obtained fertilized egg (zygote) was in vitro cultured using a culture medium to which a neutralizing antibody of a candidate factor or an antagonist of a specific receptor was added, and the blastocyst reaching rate was determined in order to verify embryo development ability. The obtained blastocysts were embryo transplanted into pseudopregnant mice, for which the implantation rate and the offspring acquisition rate were examined, and the quality of embryos was further evaluated. Specifically, the experiment was carried out as follows.

Laboratory Animal

ICR female mice (CLEA Japan, Inc., Tokyo, Japan) were used as laboratory animals. The mice were bred at a room temperature of 22° C. and a humidity of 55% under light and dark environments every 12 hours. MF control diet (Oriental Yeast Co., ltd., Tokyo, Japan) was given 6 g per mouse per day. Water was allowed to be freely ingested at any time. 3-week-old mice were used as young mice, and 42-week-old mice were used as aged mice. Five mice were used in each group.

Handling and breeding of all mice conformed to standards of experimental animal facilities of St. Marianna University School of Medicine.

In Vitro Fertilization and Embryo Culture

Mice past 3 weeks and 42 weeks of age confirmed the sexual cycle by vaginal smear. 10 IU of gonadotropin (ASKA Pharmaceutical. Co., Tokyo, Japan) was intraperitoneally administered at the time of proestrus. Cumulus oocyte complexes (COCs) were collected from a fallopian tube 15 hours after administration, and precultured for 30 minutes in 100 µl TYH medium (LSI Medience corporation, Tokyo, Japan). Meanwhile, ICR male mice (10-12 weeks old) were subjected to general anesthesia with somnopentyl anesthetic (Kyoritsuseiyaku Corporation, Tokyo, Japan), and cauda epididymis was extracted. A portion of the cauda epididymis was incised, and the internal sperm was extruded and collected. The collected sperm mass was submerged in a 1.5 mL microtube containing 400 µl TYH medium, and was subjected to swim up for 10 minutes in a $CO_2$ incubator (37° C., 5% $CO_2$, 95% in air). Sperm after swim up was added to 100 µl TYH medium containing COCs to an eventual concentration of $2-3 \times 10^5$/ml and cultured in $CO_2$ incubator (37° C., 5% $CO_2$, 95% in air) for 5-6 hours. After culturing, the sperm was removed from the egg in 30 µl KSOM Medium (Merck Millipore, Darmstadt, Germany), and the number of 2 cell stage embryos was calculated at that time. A young mouse control and an aged mouse control were then transferred to another 30 µl KSOM Medium, and cultured in a $CO_2$ incubator for 4 days. Drug treatment groups were transferred to 30 µl of KSOM Medium supplemented with a CXCL5 neutralizing antibody (ab135203, abcam) with eventual concentrations of 0.1 µg/ml, 1 µg/ml, and 10 µg/ml, 30 ml KSOM Medium supplemented with a CXCR2 antagonist (2725, TOCRIS) with eventual concentrations of 10 nM and 30 nM, and 30 µl KSOM Medium supplemented with a CXCL5 neutralizing antibody and a CXCR2 antagonist, and cultured for 4 days in a $CO_2$ incubator. The blastocyst reaching rate was calculated as the number of blastocysts/the number of two cell stage embryos.

Figure 2:
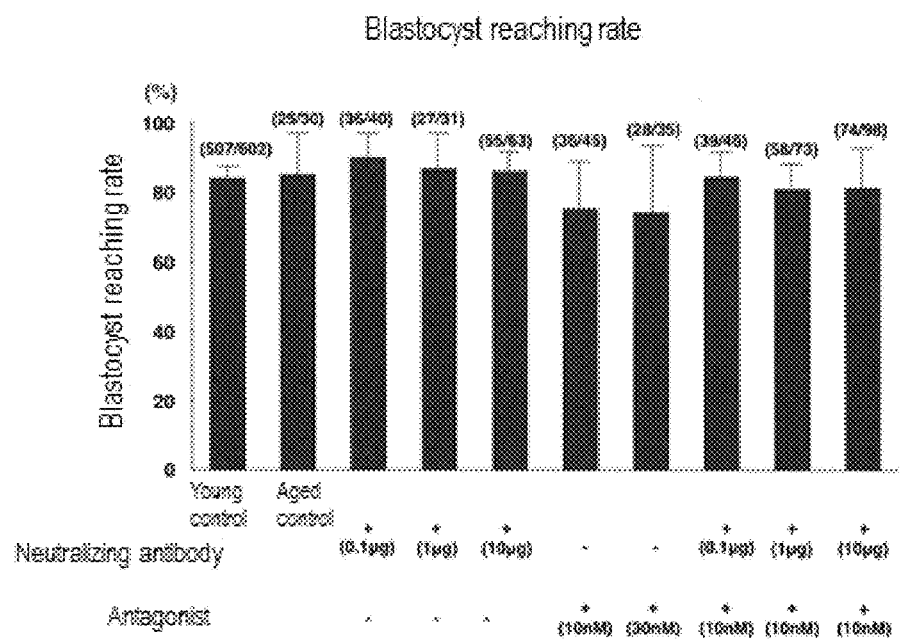
FIG. 2 shows results of the blastocyst reaching rates of embryos obtained by using a CXCL5 neutralizing antibody, a CXCR2 antagonist, or a combination thereof.

Neutralizing antibodies of CXCL5 and antagonists of specific receptors were added to fertilized eggs of aged mice at different concentrations, and no significant difference was observed between the control group and the drug treated group on the blastocyst reaching rate (FIG. 2).

Embryo Transplantation and Caesarean Section

After culturing for 4 days, an embryo reaching a blastocyst stage embryo was transplanted. Recipient mice were ICR female mice of 6 to 10 weeks of age, and mated with ICR male mice vasoligated on the day before a harvesting day, and an individual whose vaginal plug could be confirmed the next day was used. General anesthesia was given with somnopentyl anesthetic, and the uterus was exposed by a back dorsal incision. The uterus was fixed with tweezers, a 30 G injection needle (Dentronics, Tokyo, Japan) was drilled at an oviduct joint, a glass capillary with blastocyst aspirated was inserted, and the embryo was transplanted into the uterus. After transplantation, the uterus was carefully returned to the body, and the retroperitoneum and the skin were sutured. At the time of transplantation, blastocysts obtained from mice of each group were transplanted into recipient mice for each individual. Cesarean section was carried out on the 19th day with the next day of egg collection as the first day. Recipient mice were euthanized and underwent laparotomy, and the uterus was extracted and the fetus was removed. Implantation rate was calculated as the number of implantation traces/the number of embryo transplantations, and the offspring acquisition rate was calculated as the litter size/the number of implantation traces.

Figure 3A:
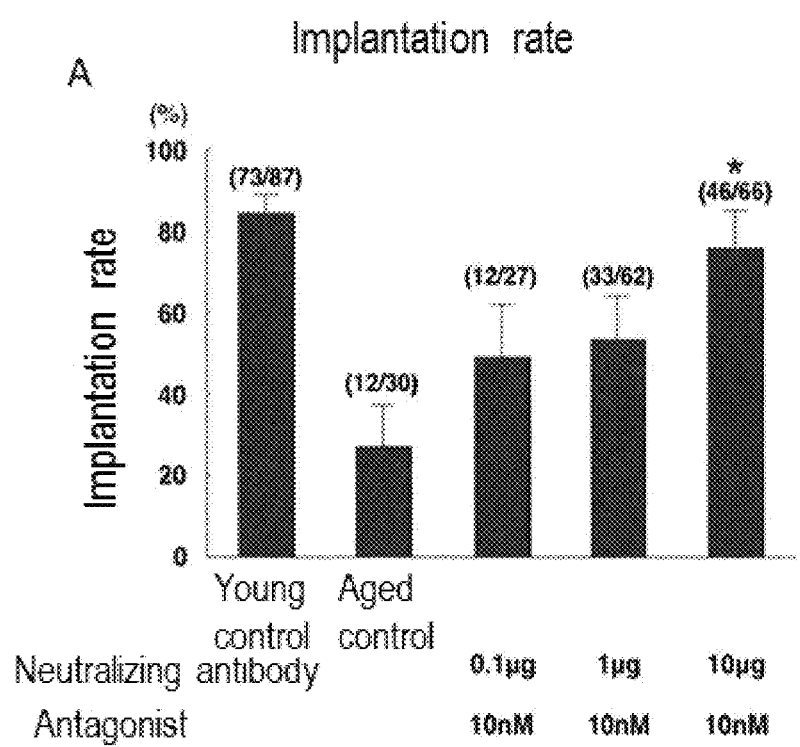
FIGS. 3A and 3B show results of transplantation of embryos obtained by using a CXCL5 neutralizing antibody and a CXCR2 antagonist in combination. A of FIG. 3 shows the implantation rate of mice in each group. B of FIG. 3 shows the offspring acquisition rate of mice in each group.
Figure 3B:
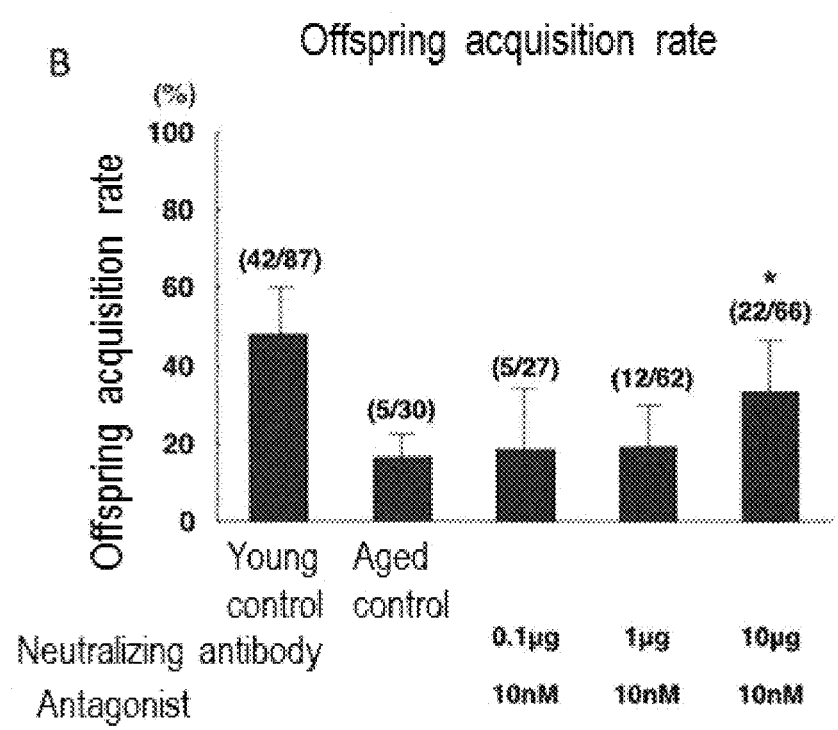
Figure 4A:
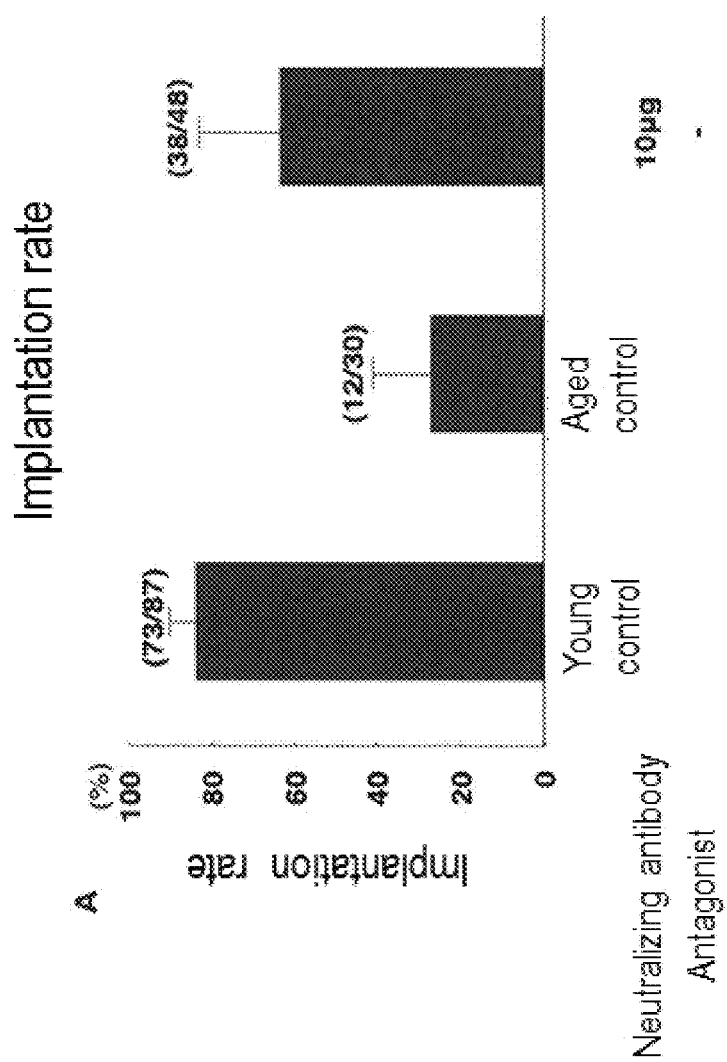
FIGS. 4A, 4B, 4C and 4D show results of transplant of embryos obtained by adding a CXCL5 neutralizing antibody and a CXCR2 antagonist each individually. A of FIG. 4 shows the implantation rate of a CXCL5 neutralizing antibody-added group. B of FIG. 4 shows the offspring acquisition rate of a CXCL5 neutralizing antibody-added group. C of FIG. 4 shows the implantation rate of a CXCR2 antagonist-added group. D of FIG. 4 shows the offspring acquisition rate of a CXCR2 antagonist-added group.
Figure 4B:
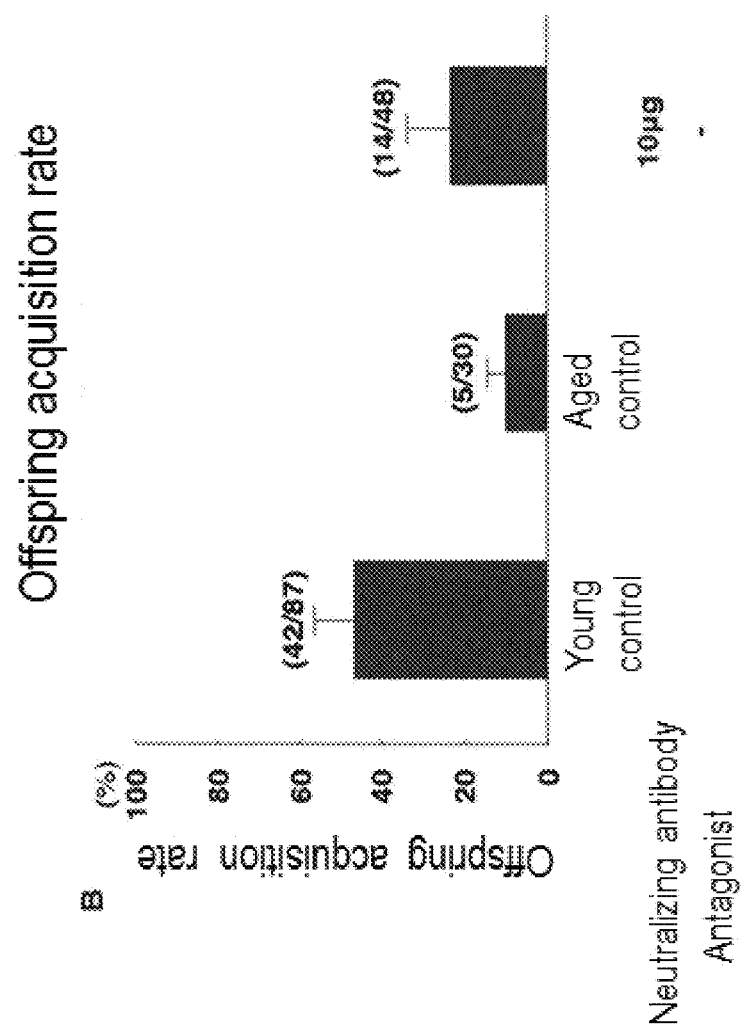
Figure 4C:
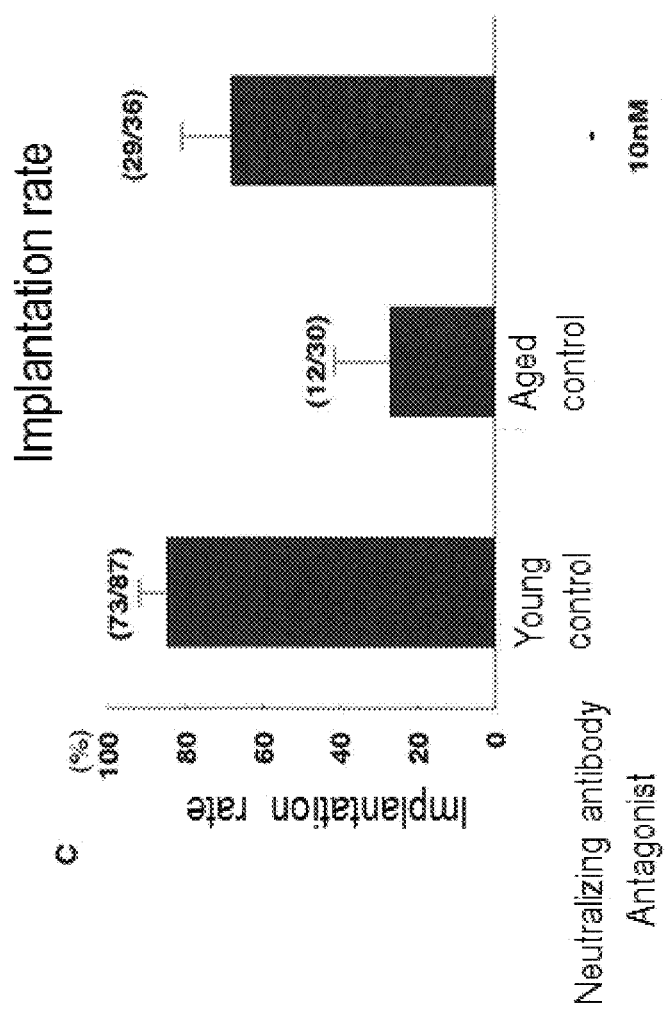
Figure 4D:
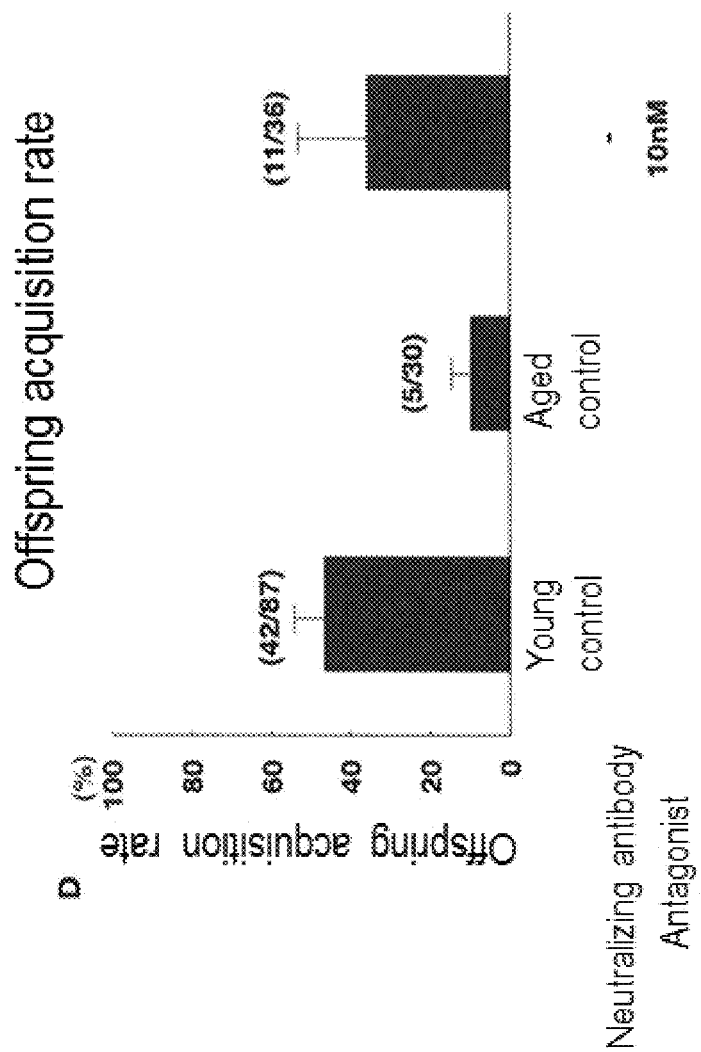

When blastocysts in the control group and the drug treated group were transplanted into pseudopregnant mice, the implantation rate was considerably improved in the neutralizing antibody+antagonist-added group (One-way ANNOVA followed by Tukey-Kramer test, *P<0.05 vs. control, FIG. 3). Significant difference was observed between the aged control and the neutralizing antibody (10 μg/ml)+antagonist (10 nM) added group. The offspring acquisition rate significantly increased in the neutralizing antibody (10 μg/ml)+antagonist (10 nM)-added group (FIG. 3).

Even in the group to which only the neutralizing antibody (10 μg/ml) was added and the group to which only the antagonist (10 nM) was added, both the implantation rate and the offspring acquisition rate tended to be higher in the drug treated group (FIG. 4).

Example 3

In the in vitro culture system of young mouse embryo, whether or not there was a change in blastocyst reaching rate, implantation rate, offspring acquisition rate by adding the candidate factor was examined using a similar method to Example 2. Expression in the embryos of aging markers p16, p21, p53, PAI-1, and IL-6 was measured, and whether or not cell aging was induced was investigated. Specifically, the experiment was carried out as follows.

Based on the method described in Example 2, in vitro fertilization and embryo culture were performed on young mice. Note that the control group was transferred to 30 μl KSOM Medium, the drug treated group was transferred to 30 μl KSOM Medium supplemented with CXCL5 (ab9803, abcam) heat-denatured (95° C., 5 min) at an eventual concentration of 1,000 nM and CXCL5 at eventual concentrations of 100 nM, 300 nM, 1,000 nM, and cultured in a $CO_2$ incubator for 4 days. The blastocyst reaching rate was then calculated.

Figure 5:
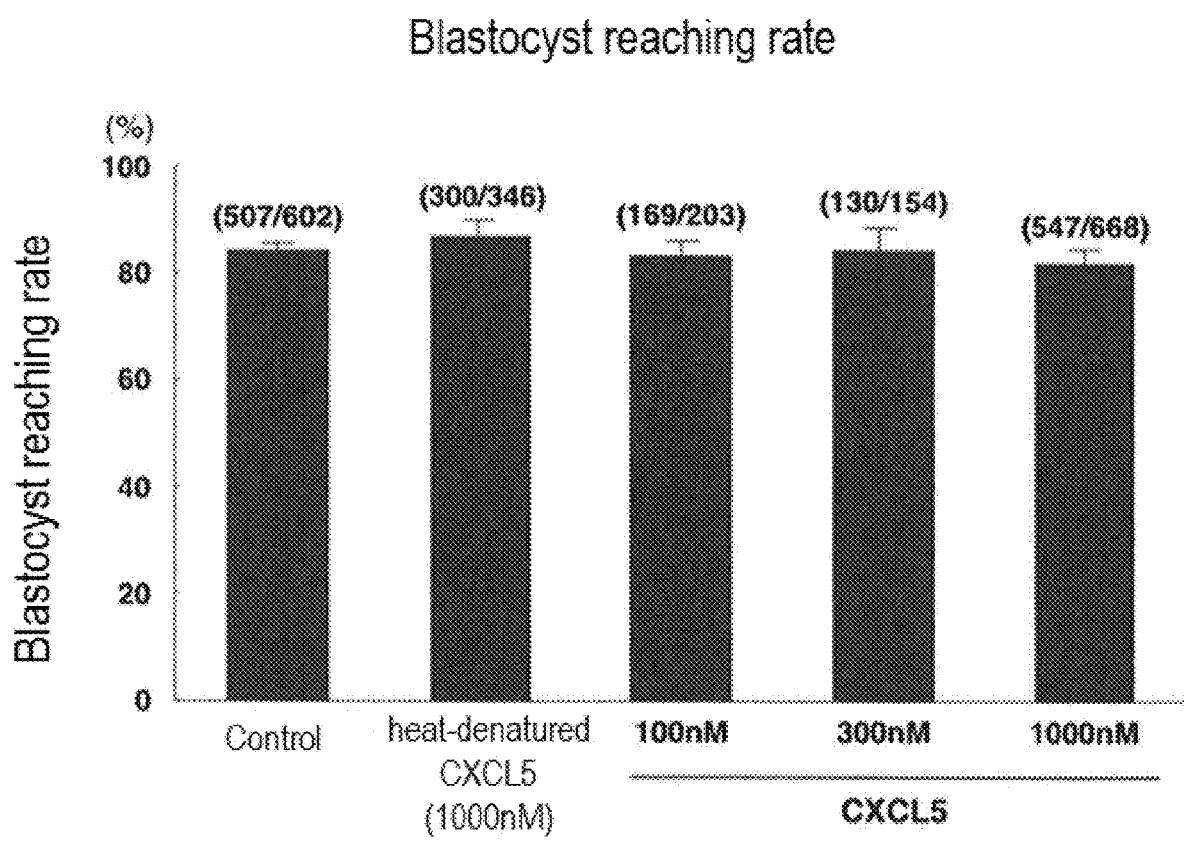
FIG. 5 shows results of the blastocyst reaching rate of embryos obtained by adding CXCL5 to young mice.

CXCL5 and heat-denatured CXCL5 were added to fertilized eggs of young mice and cultured. As a result, the blastocyst reaching rate was not significantly different from the non-added control group (FIG. 5).

Based on the method described in Example 2, blastocysts of the control group and the drug treated group were transplanted into pseudopregnant mice. The implantation rate and the offspring acquisition rate were then calculated.

Figure 6A:
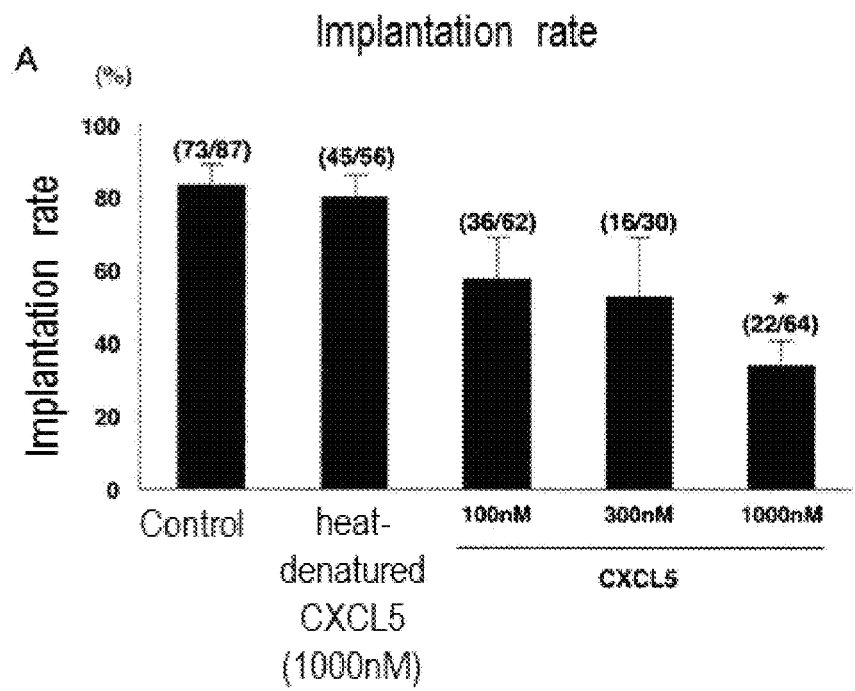
FIGS. 6A and 6B show results of transplant of embryos obtained by adding CXCL5 to young mice. A of FIG. 6 shows the implantation rate of mice in each group. B of FIG. 6 shows the offspring acquisition rate of mice in each group.
Figure 6B:
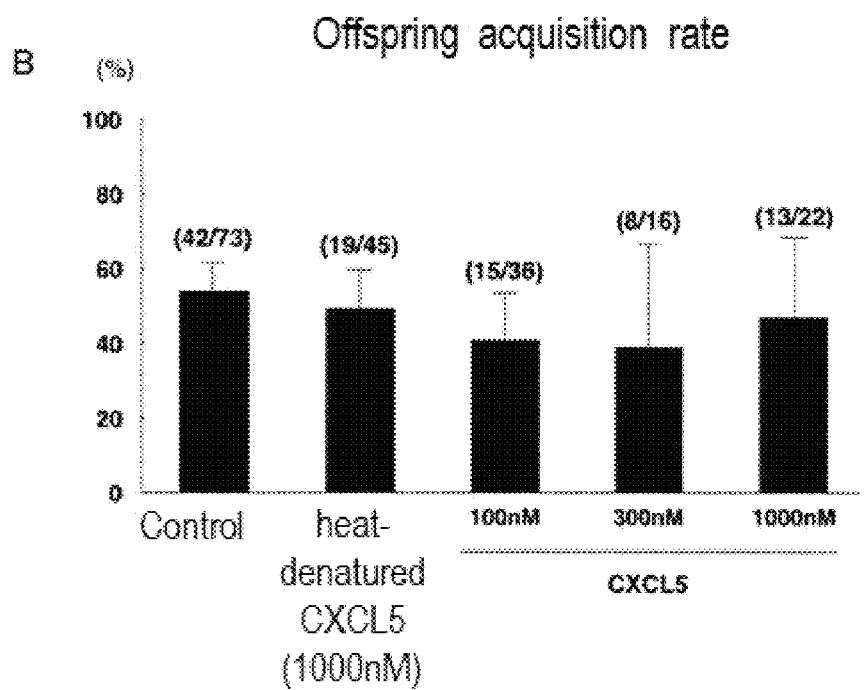
Figure 7A:
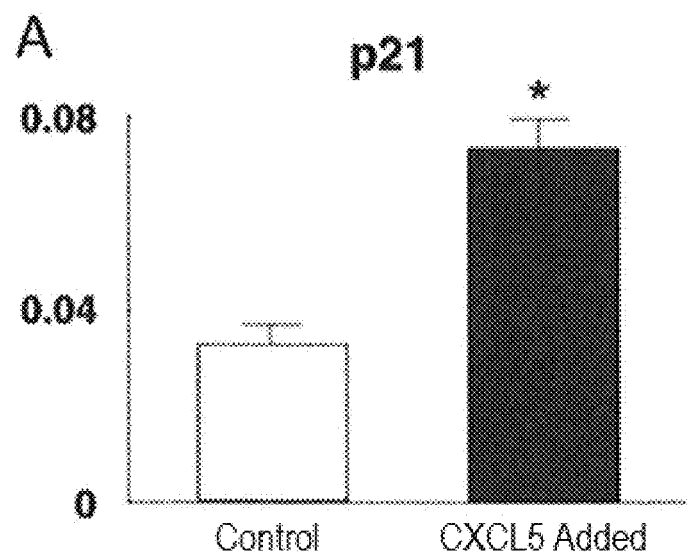
FIGS. 7A, 7B, 7C and 7D show results of expression levels of aging markers in embryos obtained by adding CXCL5 to young mice. A of FIG. 7 shows the expression level of p21. B of FIG. 7 shows the expression level of p53. C of FIG. 7 shows the expression level of PAI-1. D of FIG. 7 shows the expression level of IL-6.
Figure 7B:
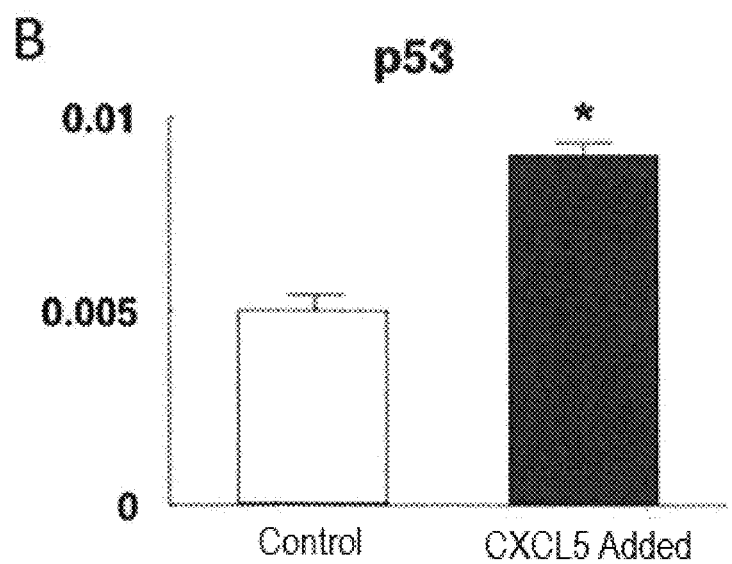
Figure 7C:
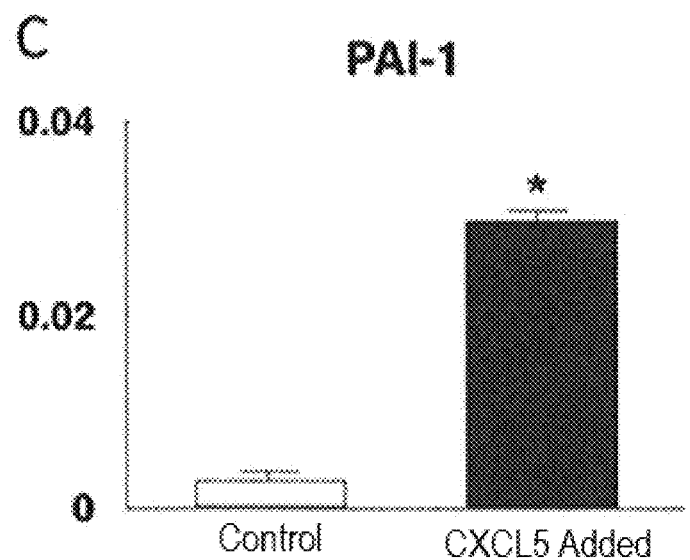
Figure 7D:
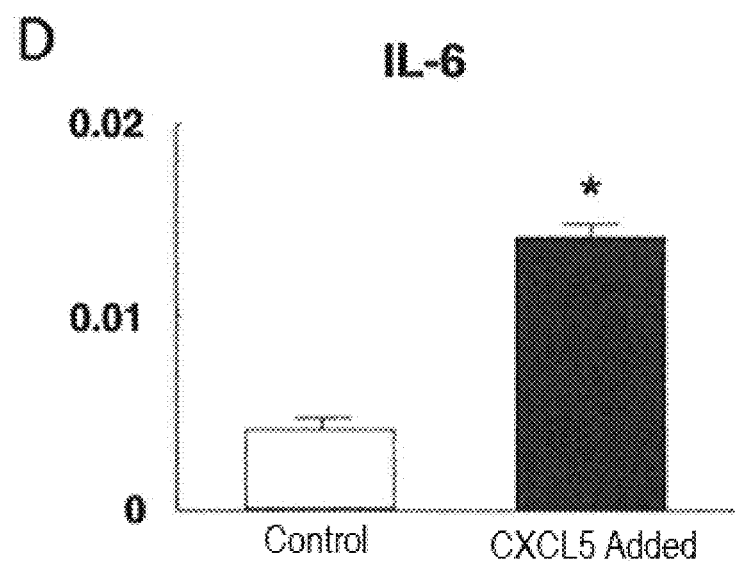

When blastocysts obtained by adding CXCL5 and heat-denatured CXCL5 were transplanted into pseudopregnant mice, the implantation rate decreased in the group to which CXCL5 was added (One-way ANNOVA followed by Tukey-Kramer test, *P<0.05 vs. control, FIG. 6). In the group to which CXCL5 was added at 1,000 nM, a significant difference was observed with the non-addition control group. There was no significant difference in the offspring acquisition rate with the control group (One-way ANNOVA followed by Tukey-Kramer test, * P<0.05 vs control, FIG. 6). There was no significant difference between the heat-denatured CXCL5-added group and the control group in both the implantation rate and the offspring acquisition rate.

Expression levels of aging markers (p16, p21, p53, PAI-1, IL-6) in embryos to which CXCL5 was added (n=30) were measured using Realtime RT-PCR. Although there was no significant difference in the expression level of p16, there was a significant increase in expression level of p21, p53, PAI-1, IL-6 (T-test, * P<0.05 vs control, FIG. 7).

Example 4

Concentrations of candidate factors in young and aged mice were measured in a serum and an ovary tissue, and whether or not the candidate factors were useful as a biomarker capable of predicting aging of an embryo was evaluated. Specifically, the experiment was carried out as follows.

Figure 8A:
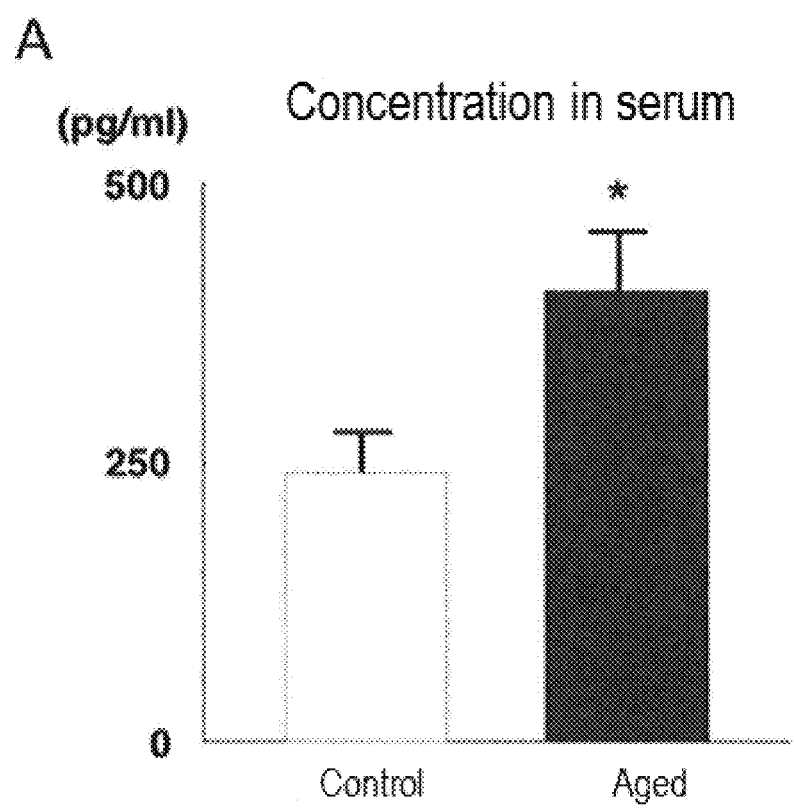
FIGS. 8A and 8B show measurement results of the concentration of CXCL5 in serum and ovary of aged and young mice. A of FIG. 8 shows the concentration in the serum. B of FIG. 8 shows the concentration in the ovary.
Figure 8B:
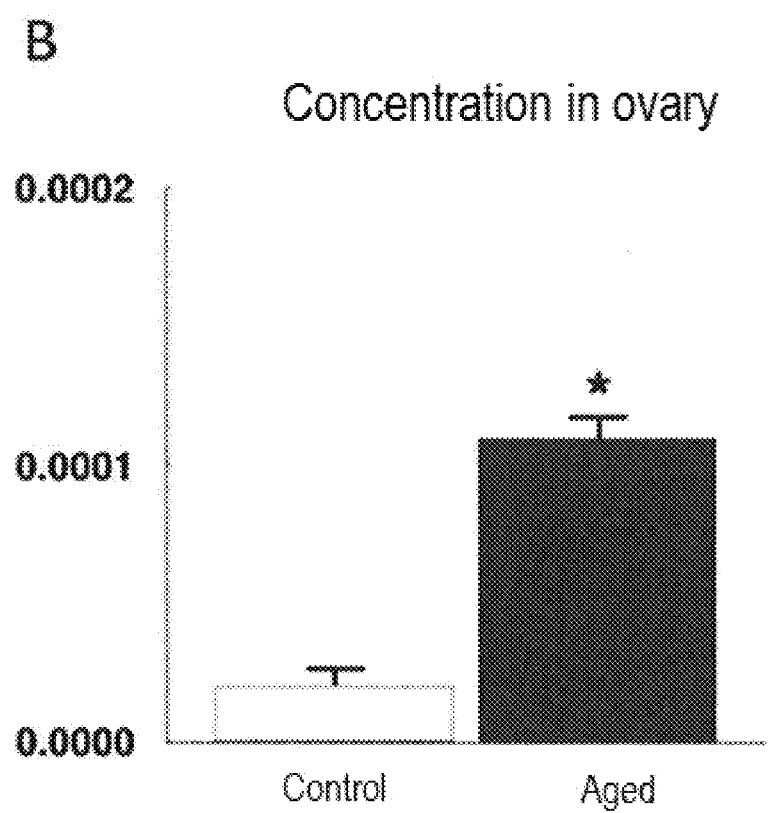

Prior to in vitro fertilization in Example 2, a serum and an ovarian tissue were collected for young mice and aged mice, respectively. The concentrations of CXCL5 in the serum and the ovary were measured using ELISA. The concentration of CXCL5 in the serum and the ovary of aged mice was significantly higher than that in young mice (T-test, * P<0.05 vs control, FIG. 8). The tendency of the concentration of CXCL5 in the serum correlated with the tendency of the concentration of CXCL5 in the ovary, and it was found that the concentration of CXCL5 in the ovary can be predicted from the concentration of CXCL5 in the serum.

It was found that inhibition of CXCL5-CXCR2 signal in aged embryo improved the quality of an egg, a fertilized egg, and an embryo deteriorated due to aging, and had an action for increasing the pregnancy rate and fertility rate in in vitro fertilized embryo transplantation or the like. It was found that CXCL5 induced aging of an embryo, and the concentration thereof in the serum was useful as an aging marker for an egg, a fertilized egg, and an embryo.

INDUSTRIAL APPLICABILITY

The present invention can be applied to medicines, medical devices, research reagents and the like.

The invention claimed is:

1. A method for improving a quality of an egg, a fertilized egg, and/or an embryo, comprising;
administering a substance that inhibits signal transmission from CXCL5 to a subject in need thereof, wherein the substance that inhibits signal transmission from CXCL5 is an anti-CXCL5 antibody or fragment thereof, an anti-CXCR2 antibody or fragment thereof, or a CXCR2 antagonist, wherein the CXCR2 antagonist is 1-(2-bromophenyl)-3-(2-hydroxy-4-nitrophenyl) urea, wherein the quality of the egg, the fertilized egg, and/or embryo is confirmed by implantation rate and/or offspring acquisition rate, and wherein the quality of the egg, the fertilized egg, and/or embryo is improved as compared to an egg, fertilized egg, and/or embryo that is not contacted with the substance.

2. The method according to claim 1, wherein the quality of an egg, a fertilized egg, and/or an embryo is deteriorated due to aging.

3. A method of predicting aging of an egg, a fertilized egg, and/or an embryo, comprising;
   measuring a concentration of CXCL5 in a serum or an ovarian tissue isolated from a subject, comparing the concentration of CXCL5 with a cutoff value, determining a presence or absence of aging of an egg, a fertilized egg, and/or an embryo by using the concentration of CXCL5 as an index, and treating the subject in which the presence of aging of an egg, a fertilized egg, and/or embryo is confirmed comprising administering to the subject a substance that inhibits signal transmission from CXCL5, wherein the egg, fertilized egg, and/or embryo is determined as "aged" if the concentration of CXCL5 is higher than the cutoff value, wherein the egg, fertilized egg, and/or embryo is determined as "not aged" if the concentration of CXCL5 is the same as or lower than the cutoff value, and wherein the substance that inhibits signal transmission from CXCL5 is an anti-CXCL5 antibody or fragment thereof, an anti-CXCR2 antibody or fragment thereof, or a CXCR2 antagonist, and wherein the CXCR2 antagonist is 1-(2-bromophenyl)-3-(2-hydroxy-4-nitrophenyl)urea.

4. The method according to claim 1, wherein the subject in need thereof is human.

5. The method according to claim 1, wherein the method is for improving a blastocyst reaching rate, an implantation rate, an offspring acquisition rate, a miscarriage rate, or pregnancy rate/fertility rate.

* * * * *